US010548515B2

(12) United States Patent
Pan et al.

(10) Patent No.: US 10,548,515 B2
(45) Date of Patent: Feb. 4, 2020

(54) METHOD FOR GENERATING PERSONAL IDENTIFICATION INFORMATION USING AN ELECTROCARDIOGRAM AND METHOD FOR IDENTIFYING A PERSON USING THE PERSONAL IDENTIFICATION INFORMATION

(71) Applicant: INDUSTRY-ACADEMIC COOPERATION FOUNDATION CHOSUN UNIVERSITY, Gwangju (KR)

(72) Inventors: Sung-Bum Pan, Gwangju (KR); Gyu-Ho Choi, Gwangju (KR); Hae-Min Moon, Gwangju (KR); Youn-Tae Kim, Daejeon (KR); Keun-Chang Kwak, Gwangju (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 392 days.

(21) Appl. No.: 15/391,384

(22) Filed: Dec. 27, 2016

(65) Prior Publication Data
US 2018/0098719 A1 Apr. 12, 2018

(30) Foreign Application Priority Data
Oct. 12, 2016 (KR) .................. 10-2016-0132046

(51) Int. Cl.
*A61B 5/117* (2016.01)
*H04L 29/06* (2006.01)
*G06K 9/00* (2006.01)
*G06K 9/62* (2006.01)
*A61B 5/04* (2006.01)
*A61B 5/0456* (2006.01)
*G06F 21/32* (2013.01)

(52) U.S. Cl.
CPC .......... *A61B 5/117* (2013.01); *A61B 5/04012* (2013.01); *A61B 5/0456* (2013.01); *G06F 21/32* (2013.01); *G06K 9/00885* (2013.01); *G06K 9/6247* (2013.01); *H04L 63/0861* (2013.01); *G06K 2009/00939* (2013.01)

(58) Field of Classification Search
CPC .......................... A61B 5/117; A61B 5/04012
USPC ....................................................... 600/509
See application file for complete search history.

(56) References Cited

FOREIGN PATENT DOCUMENTS

KR 10-2012-0131043 A 12/2012

OTHER PUBLICATIONS

Korean Office Action dated Feb. 8, 2017, issued by the Korean Intellectual Property Office in corresponding application KR 10-2016-0132046.

*Primary Examiner* — Nadia A Mahmood
(74) *Attorney, Agent, or Firm* — Stein IP, LLC

(57) ABSTRACT

Disclosed are a method for generating personal identification information using an electrocardiogram and a method for identifying a person using the personal identification information. The methods dramatically increase an identification rate by using two-dimensional image data converted from an electrocardiogram signal as personal identification information, and enable real-time identification by reducing a calculation amount by converting only a single electrocardiogram cycle into the two-dimensional image data.

14 Claims, 8 Drawing Sheets

| Number of People | Train data | Test Data | Euclidean | |
|---|---|---|---|---|
| | | | PCA | PCA+LDA |
| 10 | 10 | 100 | 94.2% | 97.7% |
| 10 | 30 | 100 | 94.8% | 98.1% |
| 10 | 50 | 100 | 95.2% | 98.6% |
| 10 | 70 | 100 | 95.9% | 99.1% |
| 10 | 100 | 100 | 96.6% | 99.7% |

METHOD FOR GENERATING PERSONAL IDENTIFICATION INFORMATION USING AN ELECTROCARDIOGRAM AND METHOD FOR IDENTIFYING A PERSON USING THE PERSONAL IDENTIFICATION INFORMATION

BACKGROUND OF THE INVENTION

1. Field of the Invention

The present invention relates to a method for generating personal identification information using an electrocardiogram and a method for identifying a person using the personal identification information. More particularly, the present invention relates to a method for generating personal identification information from an electrocardiogram signal and a method for identifying a person using the personal identification information, the methods dramatically increasing an identification rate by using two-dimensional image data converted from an electrocardiogram signal as personal identification information and enabling real-time identification by reducing a calculation amount by converting only data of a single electrocardiogram cycle into the two-dimensional image data.

2. Description of the Related Art

Personal identification is broadly used in daily life or in industries in which a password is required. That is, it is conducted for personal authentication when a person wants to have access to buildings, banking systems, or smart electronic devices in which security is a critical issue.

Conventional personal identification methods include a face recognition method, a fingerprint recognition method, and an iris recognition method. Those methods extract characteristics of a person from a facial image, a fingerprint, and an iris image of a person, obtained with the use of an optical sensor of a camera to identify the person.

These conventional personal identification methods utilizing a facial image, a fingerprint, and an iris image have the following disadvantages. Those methods are vulnerable to a variety of security issues because facial images, fingerprints, or iris images of the absent or the deceased can be used for illegal authentication. Moreover, it is difficult to identify a person in real time using those methods because those methods require processing a large amount of data.

As a solution to this problem, Korean Patent No. 10-0946766 discloses the construction of a personal identification device for identifying a person by using electrocardiogram data.

This personal identification device utilizing electrocardiogram data has an advantage that only an interested person can be authenticated because the electrocardiogram of a person cannot be reproduced or duplicated by other people.

However, the conventional personal identification device utilizing electrocardiogram data also has a problem that it is difficult to perform real-time identification because it takes time to process a large amount of data that is inevitably produced from electrocardiogram. That is, to obtain an electrocardiogram, a plurality of leads attached to the chest of a person generates their own signals, the signals are projected in a three-dimensional space to produce a vector electrocardiogram, and the vector electrocardiogram is stored and recognized as personal identification information. For this reason, a large amount of data is produced and processed to perform identification, so that personal identification cannot be performed in real time.

SUMMARY OF THE INVENTION

Accordingly, the present invention has been made keeping in mind the above problems occurring in the prior art, and an object of the present invention is to provide a method for generating personal identification information (hereinafter, also referred to as a personal identification information generation method) and a method for identifying a person (hereinafter, also referred to as personal identification method), the methods dramatically increasing an identification rate by using two-dimensional image data converted from an electrocardiogram signal as personal identification information and enabling real-time identification by reducing a data calculation amount by converting data of only a single electrocardiogram cycle into two-dimensional image data.

In order to accomplish the objects of the present invention, according to one aspect, there is provided a personal identification information generation method for generating personal identification information from an electrocardiogram signal using a computer, the method including: receiving an electrocardiogram signal; converting the electrocardiogram signal into two-dimensional image data; and generating personal identification information from the two-dimensional image data and storing the generated personal identification information.

In the preferred embodiment, the personal identification information generation method may further include extracting a single-cycle electrocardiogram signal corresponding to only a single electrocardiogram cycle composed of P, Q, R, S, and T waves, from the electrocardiogram signal received in the receiving of the electrocardiogram signal, wherein the two-dimensional image data may be generated by converting the single-cycle electrocardiogram signal.

In the preferred embodiment, the single-cycle electrocardiogram signal may be extracted by detecting a peak of the R wave and extracting an electrocardiogram signal for a predetermined period of time before and after the peak of the R wave.

In the preferred embodiment, the personal identification information generation method may further include eliminating baseline variation noise from the electrocardiogram signal before extracting the single-cycle electrocardiogram signal.

In the preferred embodiment, the converting of the electrocardiogram signal into the two-dimensional image data means a process of converting the single-cycle electrocardiogram signal into the two-dimensional image data, and the converting of the electrocardiogram signal into the two-dimensional image data includes: generating a background image having a predetermined size; and generating the two-dimensional image data by projecting the single-cycle electrocardiogram signal on the background image.

In the preferred embodiment, the background image may have a width corresponding to the number of data items of the single-cycle electrocardiogram signal and a height corresponding to the sum of a maximum value of the single-cycle electrocardiogram signal, a minimum value of the single-cycle electrocardiogram signal, and a correction value.

In the preferred embodiment, the height of the background image may be equal to the sum of a product of 100 and an absolute value of S wave amplitude, a product of 100 and R wave amplitude, and the correction value, as shown in the following Equation 1.

$$\text{Image height} = (|S \text{ wave amplitude}| \times 100) + (R \text{ wave amplitude} \times 100) + \alpha \quad \text{[Equation 1]}$$

wherein, the image height is the height of the background image, the S wave amplitude is the amplitude at the peak of the S wave, and the R wave amplitude is the amplitude at the peak of the R wave.

In the preferred embodiment, the correction value may be set to 50 corresponding to amplitude of 0.5 V of the electrocardiogram signal.

In the preferred embodiment, the projecting of the single-cycle electrocardiogram signal on the background image may be performed by calculating a value for each row coordinate by adding a product of 100 and an amplitude of the single-cycle electrocardiogram signal that changes with time, a product of 100 and an absolute value of the S wave amplitude, and a correction value of 50 as shown in Equation 2, and plotting on positions corresponding to the values of the row coordinates, in the background image, $$\text{Coordinate of row} = (\text{electrocardiogram amplitude} \times 100) + (|S \text{ wave amplitude}| \times 100) + 50 \quad \text{[Equation 2]}$$

wherein, the coordinate of row means a value for a row coordinate.

In the preferred embodiment, a single-cycle electrocardiogram signal image may be generated by performing interpolation such that values for neighboring row coordinates in the background image are consecutive to each other, and the two-dimensional image data is generated by binarizing the single-cycle electrocardiogram signal image.

In the preferred embodiment, the two-dimensional image data may be generated by reducing the single-cycle electrocardiogram signal to a predetermined size.

In the preferred embodiment, the two-dimensional image data may undergo dimensionality reduction using principal component analysis (PCA) and linear discriminant analysis (LDA), to produce image features.

In order to accomplish the objects of the invention, according to another aspect, there is provided a computer program stored in a recording medium, the computer program instructing a computer to execute the personal identification information generation method.

In addition, in order to accomplish the objects of the invention, according to a further aspect, there is provided a method for identifying a person (also referred to as personal identification method) using the personal identification information generation method, the personal identification method including: generating personal identification information of each person (hereinafter, referred to as first personal identification information) and storing the first personal identification information in a database; receiving an electrocardiogram signal of a person to be identified; generating personal identification information (hereinafter, referred to as second personal identification information) from an electrocardiogram signal of the person to be identified, using the personal identification information generation method; and performing identification by comparing the second personal identification information with each information item of the first personal identification information and determining which information item of the first personal identification information matches the second personal identification information.

In order to accomplish the objects of the present invention, according to a yet further aspect, there is provided a computer program stored in a medium, the computer program causing a computer to execute the personal identification method.

The present invention has the following advantages.

According to the personal identification information generation method using an electrocardiogram and the personal identification method using the generated personal identification information of the present invention, it is possible to dramatically improve an identification rate by using two-dimensional image data converted from an electrocardiogram signal as personal identification information, and to identify a person in real time by converting and calculating only a single cycle of electrocardiogram signal into the two-dimensional image to be used as the personal identification information.

In addition, according to the personal identification information generation method using an electrocardiogram and the personal identification method using the generated personal identification information of the present invention, since two-dimensional image data obtained through dimensionality reduction using principle components analysis (PCA) and linear discriminant analysis (LDA) is used as image feature, a calculation amount can be reduced and an identification rate can be increased.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Although most of the terms used herein have the same meaning as commonly understood by ordinary people, some terms herein are specifically defined by the applicant. When terms used herein are different from the commonly understood meaning, the terms will be interpreted as having a meaning that is consistent with their meaning in the context of the related art and the present disclosure.

Hereinafter, the technical configuration of the present invention will be described with reference to preferred embodiments illustrated in the accompanying drawings.

However, the preferred embodiments are disclosed only for illustrative purposes and thus should not be construed as limiting the present invention. That is, the present invention can be embodied in different forms. Throughout the drawings, the same reference numerals will refer to the same or like parts.

A method for generating personal identification information according to one embodiment of the present invention includes a process of converting an electrocardiogram signal of a person into two-dimensional image data and a process of generating personal identification information using image features of the converted two-dimensional image data.

In addition, a personal identification method according to one embodiment of the present invention is a method of identifying a person using the personal identification information generated through the personal identification information generation method set forth.

The personal identification information generation method and the personal identification method according to one embodiment of the present invention are substantially executed by a computer. To this end, in a computer, a computer program for instructing the computer to execute the personal identification information generation method or the personal identification method is stored.

The computer is a computing device in broad terms, and includes a smart electronic device, an embedded system, etc. that can perform image processing, as well as a generally-known personal computer.

The computer program may be provided in the form of a computer program stored in an independent recording medium, wherein the recording medium may be a dedicated storage device specially designed for the present invention or may be a recording medium that is well-known to those ordinarily skilled in the art of computer software.

For example, the recording medium may be a hardware device specially constructed to store and execute program instructions or commands singly or in combination. Examples of the recording medium may include: an electromagnetic medium such as hard disk, floppy disk, or magnetic tape; an optical recording medium such as compact disk (CD) or digital versatile disk (DVD); a magneto-optical recording medium; and a memory device such as ROM, RAM, or flash memory.

In addition, the computer program may be a program involving any one component of program instructions or commands, local data files, and local data structure. The computer program may be machine codes derived by a compiler, or codes that are written in any programming language to be executed by a computer with the aid of an interpreter.

Hereinafter, a personal identification information generation method using an electrocardiogram and a personal identification method according to one embodiment of the present invention will be described with reference to FIG. 1.

Figure 1:
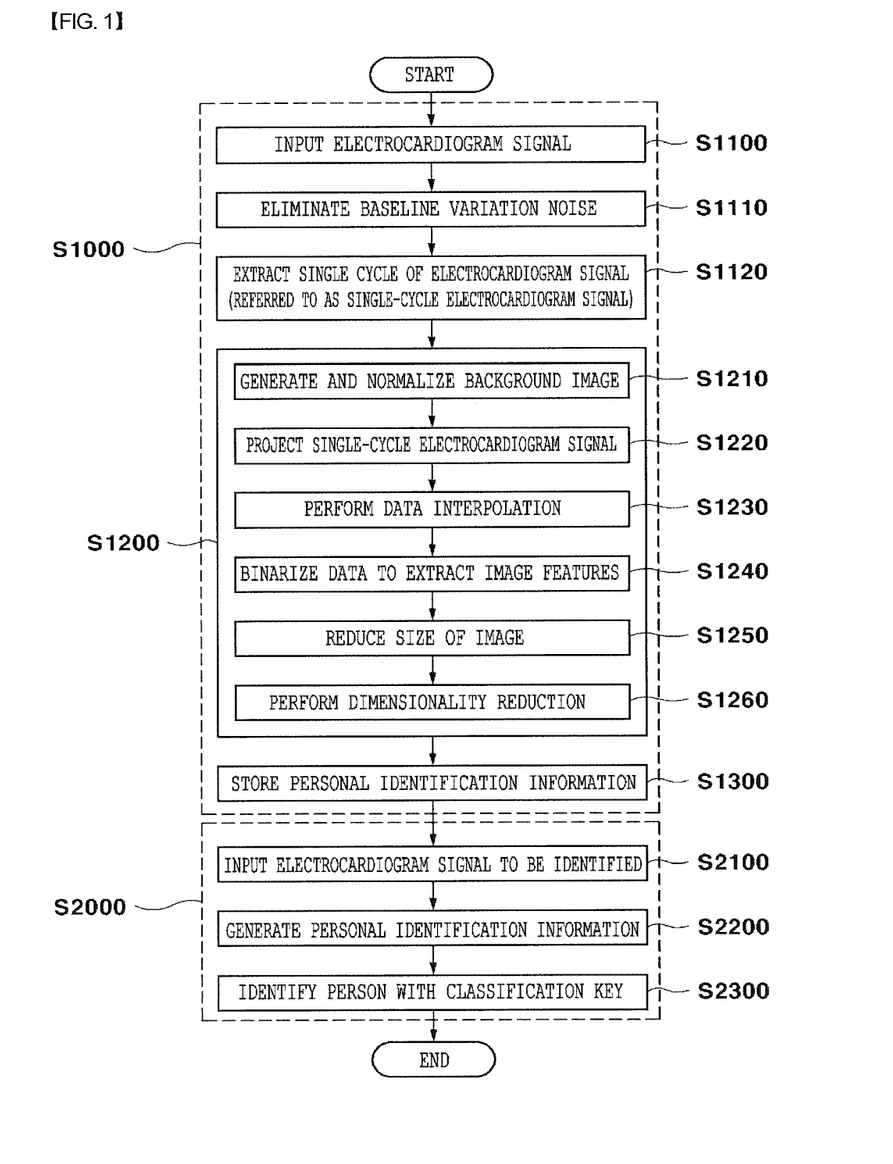
FIG. 1 is a flowchart illustrating a personal identification information generation method using an electrocardiogram and a personal identification method according to one embodiment of the present invention.

With reference to FIG. 1, the personal identification information generation method and the personal identification method according to one embodiment of the present invention includes a personal identification information generation method S1000 for generating personal identification information from an electrocardiogram signal and storing the generated personal identification information, and a personal identification method S2000 for identifying a person using the stored personal identification information.

The personal identification information generation method S1000 roughly includes the steps of: receiving an electrocardiogram signal S1100, converting the electrocardiogram signal into two-dimensional image data S1200, and storing the two-dimensional image data as personal identification information. Additionally, the personal identification information generation method S1000 may further include the steps of: eliminating baseline variation noise S1110, and extracting a single cycle of the electrocardiogram signal S1120, both of which are performed after the reception of the electrocardiogram signal.

According to the personal identification information generation method S1000, an electrocardiogram signal is first input from an electrocardiogram measuring device (S1100).

Figure 2:
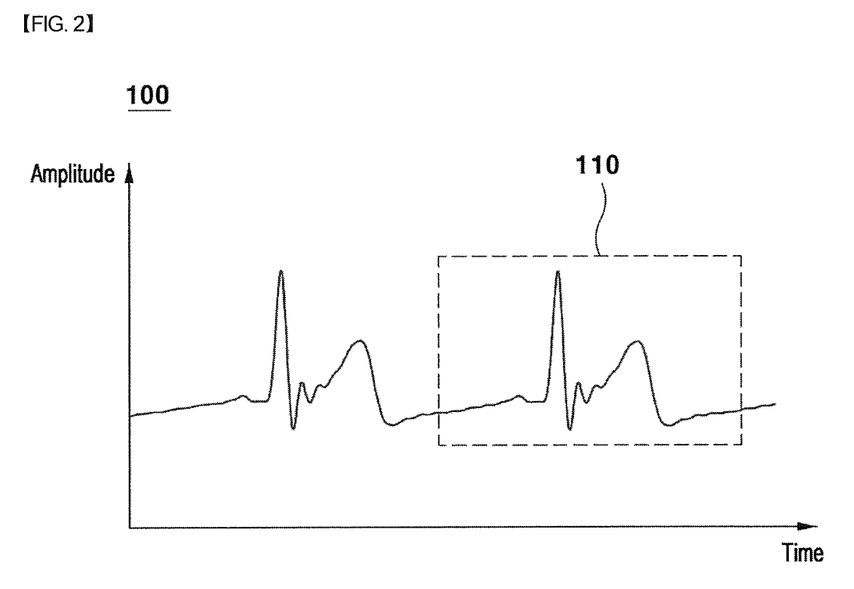
FIG. 2 is a graph illustrating an electrocardiogram signal that is used in the personal identification information generation method using an electrocardiogram and the personal identification method according to one embodiment of the present invention.

FIG. 2 shows an electrocardiogram signal 100. The electrocardiogram signal 100 is a one-dimensional analog signal and is the measure of an electrical current that is generated by a to heart muscle due to the heart beating. The electrocardiogram signal 100 is a signal measured through twelve-lead electrocardiography.

The electrocardiogram signal 100 consists of a plurality of waves that consecutively appear with time.

Next, baseline variation noise is eliminated from the electrocardiogram signal 100 (S1110).

The baseline variation noise is a low frequency noise having a frequency lower than 1 Hz among electrocardiogram noises attributable to heart beats.

In the present invention, the baseline variation noise having a frequency lower than 1 Hz is eliminated using a bandpass filter. Therefore, the electrocardiogram signal used herein has a predetermined pattern.

Next, from the noise-removed electrocardiogram signal, only one electrocardiogram cycle of the electrocardiogram signal (hereinafter, referred to as "single-cycle electrocardiogram signal") 110 is extracted (S1120).

Figure 3:
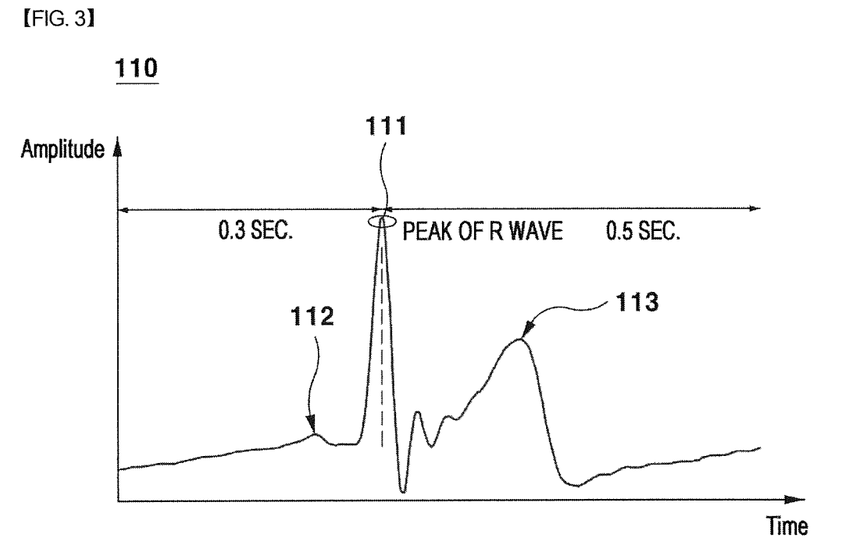
FIG. 3 is a graph illustrating a single-cycle electrocardiogram signal used in the personal identification information generation method using an electrocardiogram and the personal identification method according to one embodiment of the present invention.

With reference to FIG. 3, the single-cycle electrocardiogram signal 110 consists of 5 waves called P, Q, R, S, and T.

The single-cycle electrocardiogram signal 110 is extracted by first detecting the peak 111 of the R wave and then picking out a portion of the electrocardiogram signal, the portion including a signal measured for 0.5 seconds prior to the occurrence of the peak 111 of the R wave (signal on the left side of the peak 111 of the R wave) and a signal measured for 0.3 seconds after the occurrence of the peak 111 of the R wave (signal on the right side of the peak 111 of the R wave).

Here, the 0.5 seconds and 0.3 seconds are determined through experiments. The signal occurring for 0.5 seconds and 0.3 seconds before and after the peak of the R wave includes the P wave 112 on the left side of the R wave and the T wave 113 on the right side of to the R wave, but does not include the other cycles.

Figure 4:
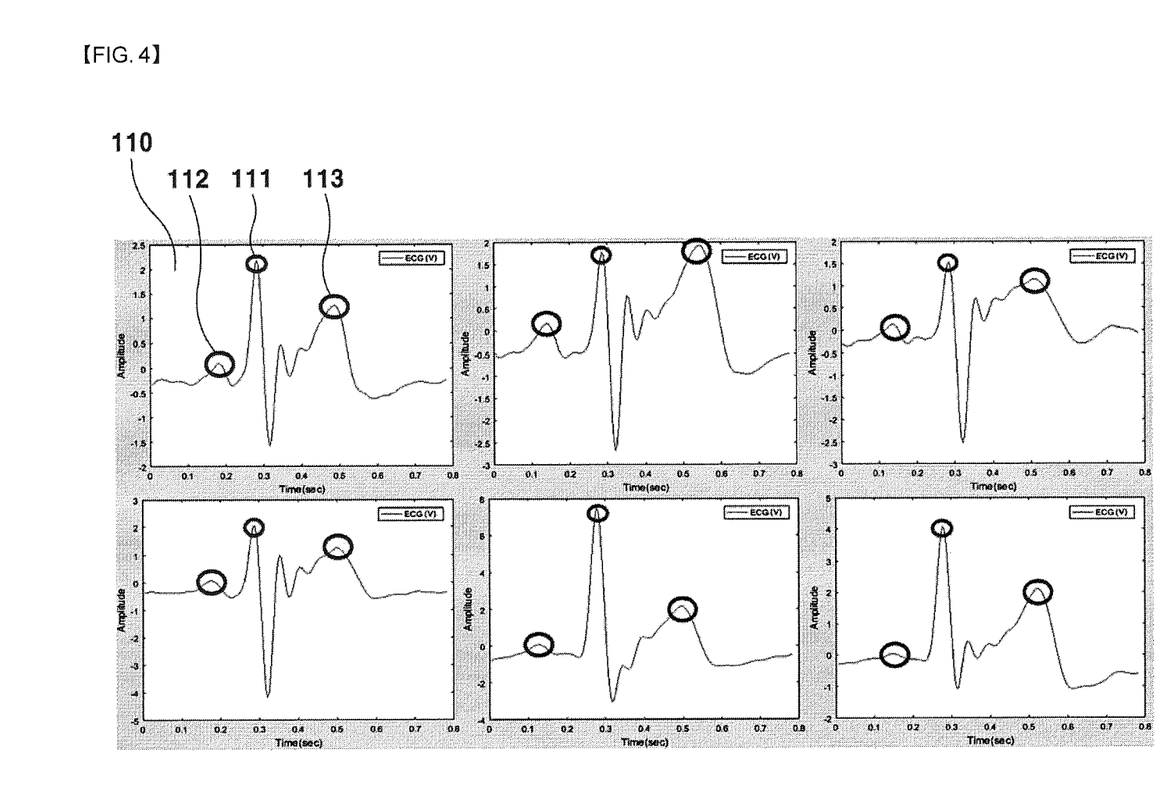
FIG. 4 shows a plurality of graphs illustrating samples of the single-cycle electrocardiogram signal obtained from six subjects, used in the personal identification information generation method using an electrocardiogram and the personal identification method according to one embodiment of the present invention.

FIG. 4 shows single-cycle electrocardiogram signals 110 of six subjects. The single-cycle electrocardiogram signal 110 of each subject is extracted to include the P wave 112 and the T wave 113 but does not include the other cycles of electrocardiogram signal.

The number of data items in the single-cycle electrocardiogram signal 110 is calculated by multiplying a sampling rate of the electrocardiogram signal 110 by an extraction time of the electrocardiogram signal, as shown in the following Mathematical Equation "a".

$$\text{the number of data items of a single cycle electrocardiogram signal} = (\text{sampling rate} \times 0.3 \text{ seconds}) + (\text{sampling rate} \times 0.5 \text{ seconds}) \quad \text{[Mathematical Equation a]}$$

When the sampling rate is 256 Hz, the single-cycle electrocardiogram signal 110 is made up of 204 data items.

A Pan_Tomkins algorithm that extracts a peak by using a bandpass filter and the fourth power operation is used to extract the peak of the R wave 111.

Next, the single-cycle electrocardiogram signal 110 is converted into two-dimensional image data (S1200).

That is, the personal identification information generation method according to one embodiment of the present invention can convert the whole electrocardiogram signal that is input, into two-dimensional image data but practically converts only a single cycle of electrocardiogram signal into two-dimensional image data to generate personal identification information. Therefore, the personal identification information generation method according to one embodiment of the present invention can reduce the amount of data to be calculated for identification and thus is advantageous in terms of real time identification because of a reduced calculation amount and time.

Next, a background image on which the single-cycle electrocardiogram signal 110 is to be projected is generated. Next, the single-cycle electrocardiogram signal 110 is normalized so that the single-cycle electrocardiogram signal 110 can be projected on the background image (S1210).

Figure 5:
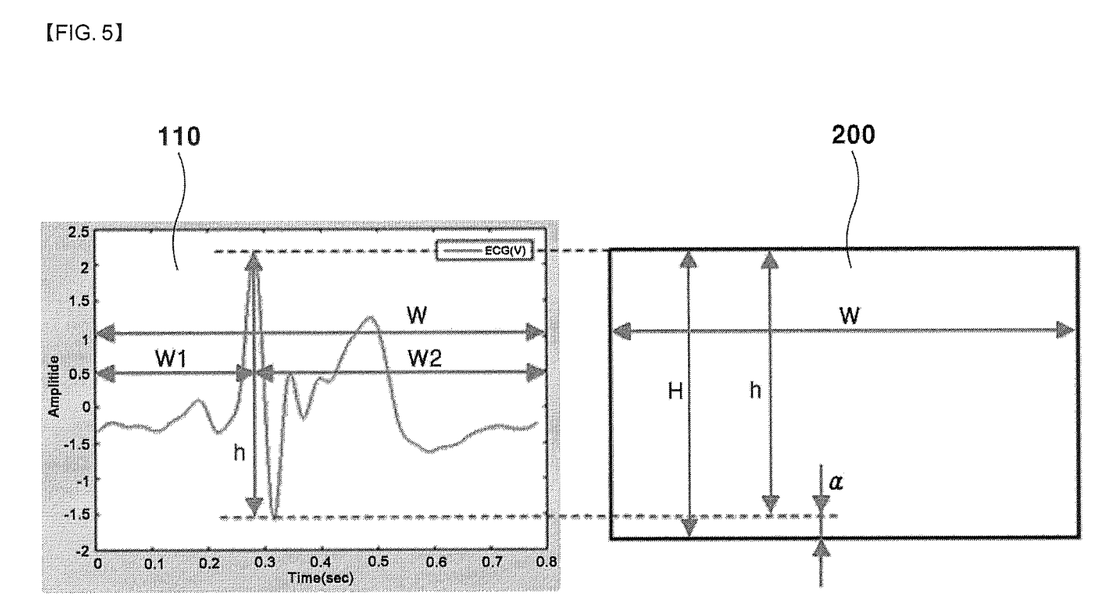
FIG. 5 is a background image used in the personal identification information generation method using an electrocardiogram and the personal identification method according to one embodiment of the present invention.

FIG. 5 shows a background image 200. The background image 200 has 204 pixels in the width W thereof so as to correspond to the data items of the electrocardiogram signal 110. The height H of the background image 200 is calculated by first subtracting a minimum value of the single-cycle electrocardiogram signal 110 from a maximum value of the single-cycle electrocardiogram signal to obtain a value (subtraction result) h and then adding a correction value a to the value h.

For example, the height of the background image 200 is the sum of a product of 100 and the absolute value of S wave amplitude (1.5 V), a product of 100 and R wave amplitude (2 V), and the correction value, as shown in the following Equation 1.

$$\text{Image height} = (|S \text{ wave amplitude}| \times 100) + (R \text{ wave amplitude} \times 100) + \alpha \quad \text{[Equation 1]}$$

Herein, the image height is the height H of the background image 200, the S wave amplitude is the amplitude at the peak of the S wave, and the R wave amplitude is the amplitude at the peak of the R wave.

In the present invention, the correction value a is set to 50 that corresponds to an amplitude of 0.5 V.

That is, according to the present invention, the correction value a is added to ensure that both the peak of the S wave and the Peak of the R wave are included within the background image 200.

Figure 6:
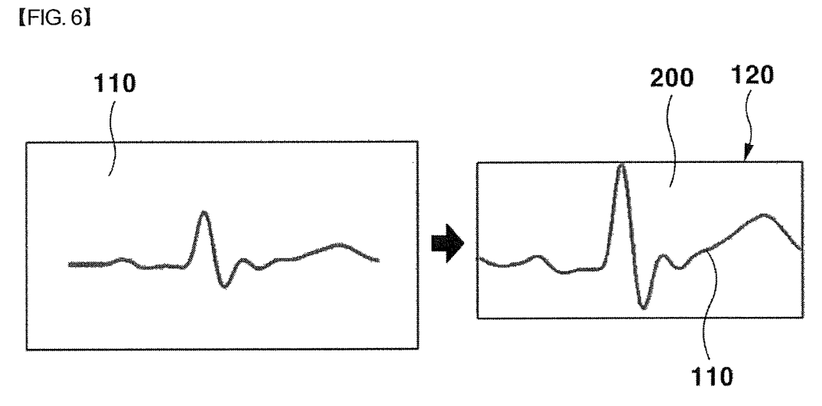
FIG. 6 is a diagram illustrating a process of normalizing the single-cycle electrocardiogram signal on the background image, in the personal identification information generation method using an electrocardiogram and the personal identification method according to one embodiment of the present invention.

In addition, FIG. 6 shows an electrocardiogram signal image 120 obtained by normalizing the single-cycle electrocardiogram signal 110 such that the size of the single-cycle electrocardiogram signal equals the size of the background image 200. The electrocardiogram signal 110 is normalized to the size of the background image 120 while maintaining the waveform thereof.

Figure 7:
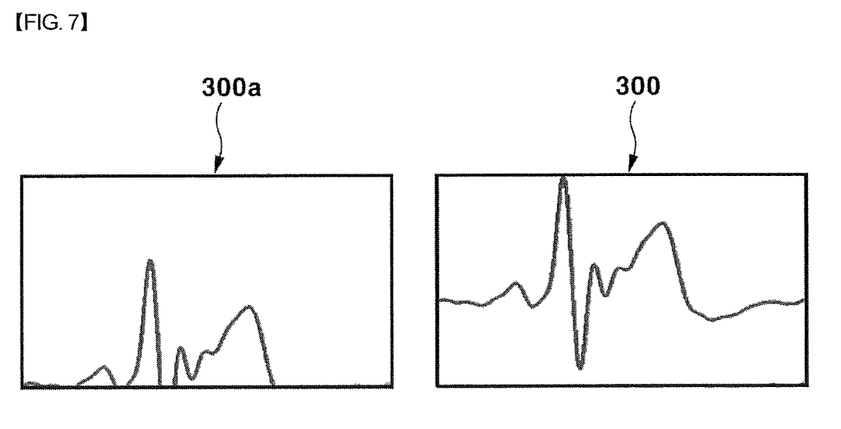
FIG. 7 is a diagram illustrating a process of projecting a single-cycle electrocardiogram signal on the background image, in the personal identification information generation method using an electrocardiogram and the personal identification method according to one embodiment of the present invention.

Next, the single cycle electrocardiogram signal 110 is projected on the background image 200 to produce two-dimensional image data 300.

In order to project the single-cycle electrocardiogram signal 110 on the background image 200, it is necessary to calculate values for row coordinates of the single-cycle electrocardiogram signal 110. Each of the values for the respective row coordinates may be the sum of a product of 100 and the amplitude (electrocardiogram amplitude) of the single-cycle electrocardiogram signal 110, a product of 100 and the absolute value of S wave amplitude, and the correction value "50", as shown in the following Equation 2.

$$\text{Coordinate of row} = (\text{electrocardiogram amplitude} \times 100) + (|S \text{ wave amplitude}| \times 100) + 50 \quad \text{[Equation 2]}$$

Next, pixel values are mapped on positions, corresponding to the row coordinates, in the background image 200. In this way, an image projection is completed.

The reason of addition of the absolute value of the S wave amplitude in the calculation of the values for the row coordinates is to prevent data loss because data items corresponding to negative amplitude values shown in the left image 300a of FIG. 7 are likely to be lost through simple projection.

The right image 200 of FIG. 7 is two-dimensional image data 300 obtained by normalizing the single-cycle electrocardiogram signal 110 and projecting it on the background image 200.

Figure 8:
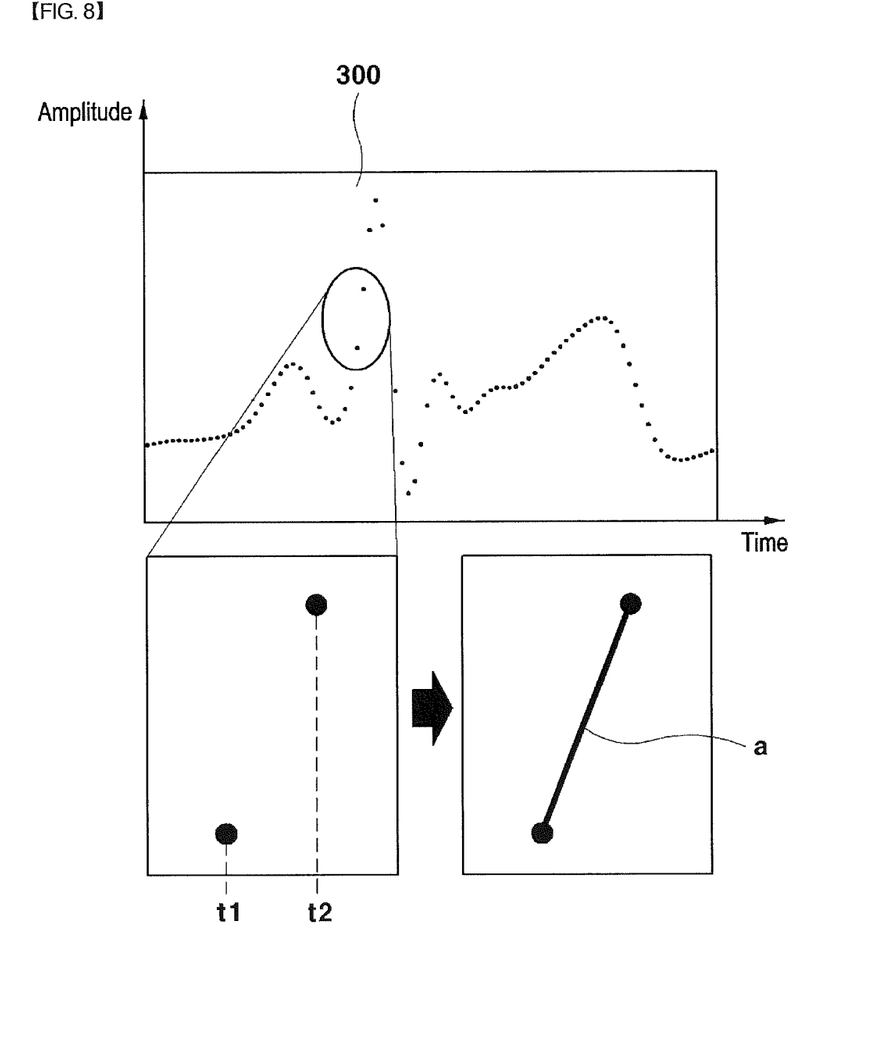
FIG. 8 shows pictures illustrating a process of interpolating two-dimensional image data used in the personal identification information generation method using an electrocardiogram and the personal identification method according to one embodiment of the present invention.

Next, data items that are lost and not present in the two-dimensional image data 300 are generated through data interpolation, so that the non-continuous electrocardiogram image becomes a continuous electrocardiogram image (S1230).

With reference to FIG. 8, since the electrocardiogram signal is voltages versus time, the electrocardiogram signal is a non-continuous signal. Therefore, when data of the electrocardiogram signal is projected on the background image, the electrocardiogram image is based on the two-dimensional image data 300 is not continuous.

In other words, there is no data at time t1 and time t2 that are consecutive.

Therefore, according to the present invention, interpolation is performed to fill data voids (voids filling, a) and thus an identification rate can be increased.

Figure 9:
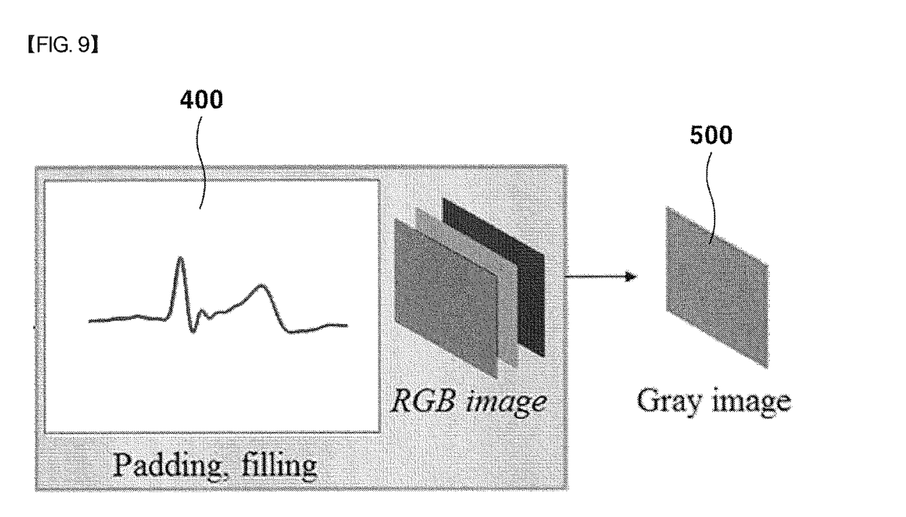
FIG. 9 shows diagrams illustrating a process of converting two-dimensional image data into a gray image in the personal identification information generation method using an electrocardiogram and the personal identification method according to one embodiment of the present invention.

The two-dimensional image data can be converted into a color image 400 as shown in FIG. 9 through pixel values padding and filling.

Next, the two-dimensional color image data 400 is converted into a gray image 500.

Next, binarization of the gray image 500 is performed to produce a binary image in which the background is displayed in white and the electrocardiogram signal is displayed in black. Therefore, the background and the electrocardiogram signal are highly contrasted with each other.

Figure 10:
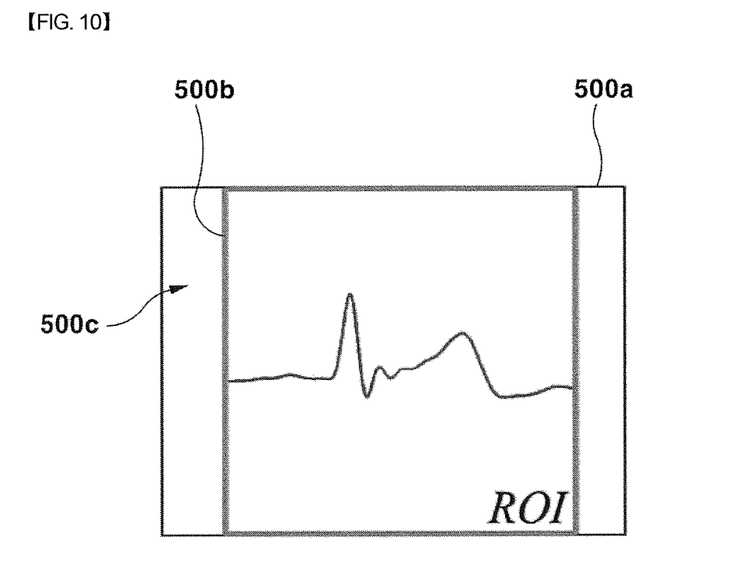
FIG. 10 is a diagram illustrating a process of binarizing the gray image in the personal identification information generation method using an electrocardiogram and the personal identification method according to one embodiment of the present invention.

Since the background image 200 is stored in an enlarged size when it is stored in a database, as shown in FIG. 10, only a region of interest (ROI) 500b, in which an electrocardiogram signal exists, is extracted from the image data 500a, and a region 500c, in which no electrocardiogram signal exists, is discarded. Then, only the ROI undergoes binarization. That is, it is preferable to reduce a calculation amount in this way.

Figure 11:
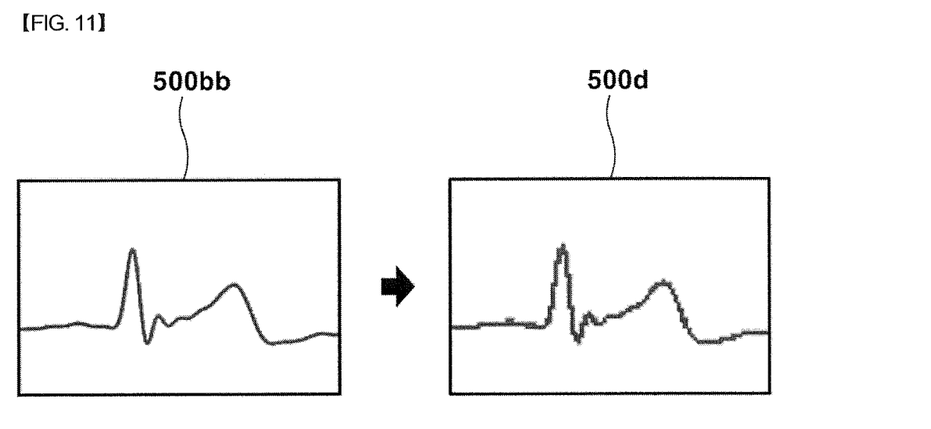
FIG. 11 shows diagrams illustrating a process of reducing the size of binarized image in the personal identification information generation method using electrocardiogram and the personal identification method according to one embodiment of the present invention.

Next, the size of the binarized two-dimensional image data 500bb is reduced (S1250).

The purpose of the size reduction process is to reduce the amount of data to be stored, resulting in an improved data processing speed.

With reference to FIG. 11, a left image 500bb is the binarized two-dimensional image data composed of 656× 675 pixels, obtained by binarizing the ROI 500b, and a right image 500d is size-reduced two-dimensional image data 500bb composed of 100×100 pixels, obtained by reducing the size of the binarized two-dimensional image data 500bb.

Next, dimensionality reduction using principal component analysis (PCA) and linear discriminant analysis (LDA) is performed with respect to the size-reduced two-dimensional image data 500d (S1260), and the two-dimensional image data (image feature) that has undergone dimensionality reduction is stored as personal identification information (S1300).

After the personal identification information is stored, identification of a person is performed (S2000).

First, an electrocardiogram signal of a person to be identified is input (S2100).

Next, personal identification information of the to-be-identified person is generated from the electrocardiogram signal (S2200).

A method of generating the personal identification information is the same as the above-described personal identification information generation method S1000.

Next, the generated personal identification information (test data) is compared with personal identification information (train data) that is preliminarily stored in a database (S2300).

Here, comparison and classification of multiple items of personal identification information are performed using the Euclidean distance formula.

Figure 12:
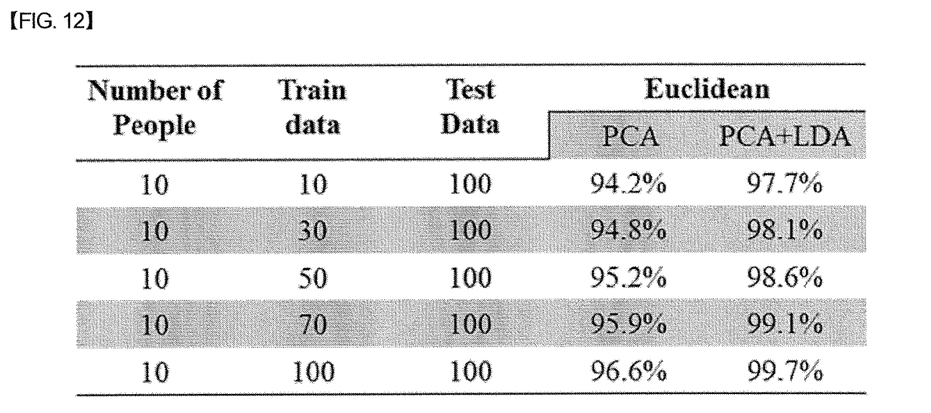
FIG. 12 is a table illustrating the identification results obtained using the personal identification information generation method using electrocardiogram and the personal identification method according to one embodiment of the present invention.

FIG. 12 is a table illustrating the identification results obtained using the personal identification information generation method using electrocardiogram and the personal identification method according to one embodiment of the present invention.

10 people participated in the test and a total of 200 items of train data were stored.

Identification of a person to be identified was performed by calculating the Euclidean distance of the personal identification information (test data) while changing the number of items of the preliminarily registered personal identification information (train data).

In conclusion, when identifying a person using the personal identification information that has undergone dimensionality reduction performed through PCA and LDA, a maximum identification rate was 99.7%. That is, the identification rate obtained by performing both of the PCA and LDA was higher than an identification rate obtained by performing only PCA.

Although the present invention has been described in conjunction with preferred embodiments thereof, it is to be understood that the present description is not intended to limit the present invention to those preferred embodiments. On the contrary, the present invention is intended to cover not only the preferred embodiments, but also various alternatives, modifications, equivalents and other embodiments that may be included within the spirit and scope of the present invention as defined by the appended claims.

What is claimed is:

1. A method for generating personal identification information from an electrocardiogram signal using a computer, the method comprising:
   receiving an electrocardiogram signal;
   extracting a single-cycle electrocardiogram signal containing P, Q, R, S, and T waves from the electrocardiogram signal after the receiving of the electrocardiogram signal;
   converting the electrocardiogram signal into two-dimensional image data; and
   generating personal identification information from the two-dimensional image data and storing the generated personal identification information,
   wherein the two-dimensional image data is generated by converting the single-cycle electrocardiogram signal.

2. The method according to claim 1, wherein the single-cycle electrocardiogram signal is extracted by detecting a peak of the R wave and picking out a portion of the electrocardiogram signal, including a first portion corresponding to a signal measured for a first period of time prior to occurrence of the peak of the R wave and a second portion corresponding to a signal measured for a second period of time after the occurrence of the peak of the R wave.

3. The method according to claim 1, further comprising:
   eliminating a baseline variation noise from the electrocardiogram signal before the extracting of the single-cycle electrocardiogram signal.

4. The method according to claim 1, wherein the converting of the electrocardiogram signal into the two-dimensional image data means a process of converting the single-cycle electrocardiogram signal into the two-dimensional image data, and wherein the converting of the electrocardiogram signal into the two-dimensional image data includes:
   generating a background image having a predetermined size; and
   generating the two-dimensional image data by projecting the single-cycle electrocardiogram signal on the background image.

5. The method according to claim 4, wherein the background image has a width corresponding to the number of data items of the single-cycle electrocardiogram signal and a height that is the sum of a maximum value and a minimum value of the single-cycle electrocardiogram signal and a correction value.

6. The method according to claim 5, wherein the height of the background image is the sum of a product of 100 and an absolute value of an amplitude of the S wave, a product of 100 and an amplitude of the R wave, and the correction value, as shown in the following Equation 1, $$\text{Image height}=(|S \text{ wave amplitude}|\times 100)+(R \text{ wave amplitude}\times 100)+\alpha \quad \text{[Equation 1]}$$

wherein, image height is the height of the background image, S wave amplitude is the amplitude at the peak of the S wave, and R wave amplitude is the amplitude at the peak of the R wave.

7. The method according to claim 6, wherein the correction value is 50 corresponding to amplitude (0.5 V) of the electrocardiogram signal.

8. The method according to claim 7, wherein the projecting of the single-cycle electrocardiogram signal on the background image is performed by calculating a value for each row coordinate by adding a product of 100 and an amplitude of the single-cycle electrocardiogram signal that changes with time, the product of 100 and the absolute value of the amplitude of the S wave, and a correction value of 50 as shown in the following Equation 2, and plotting on a position corresponding to the value of row coordinate within the background image, $$\text{Coordinate of row}=(\text{electrocardiogram amplitude}\times 100)+(|S \text{ wave amplitude}|\times 100)+50 \quad \text{[Equation 2]}$$

wherein, the coordinate of row means a value for a row coordinate.

9. The method according to claim 8, wherein a single-cycle electrocardiogram signal image is generated by performing interpolation such that values for neighboring row coordinates are consecutive to each other, and the two-dimensional image data is generated by binarizing the single-cycle electrocardiogram signal image.

10. The method according to claim 9, wherein the two-dimensional image data is generated by reducing the single-cycle electrocardiogram signal to a predetermined size.

11. The method according to claim 10, wherein to obtain image feature, the two-dimensional image data undergoes dimensionality reduction that is performed through principal component analysis (PCA) and linear discriminant analysis (LDA).

12. A computer program stored in a medium to implement the method according to claim 1 by cooperating with a computer.

13. A method for identifying a person, the method comprising:
generating multiple items of personal identification information (hereinafter, referred to as first personal identification information) using the method according claim 1 and storing the first personal identification information in a database;
receiving an electrocardiogram signal of a person to be identified;
generating personal identification information (hereinafter, referred to as second personal identification information) from the electrocardiogram signal of the person to be identified, using the method according to claim 1; and
performing identification by comparing the second personal identification information with each item of the first personal identification information and determining which item of the first personal identification information matches the second personal identification information.

14. A computer program stored in a medium to implement the method according to claim 13 by cooperating with a computer.

* * * * *